United States Patent [19]

Rothlisberger

[11] Patent Number: 4,609,624

[45] Date of Patent: Sep. 2, 1986

[54] PROCESS FOR PRODUCING ISOPROPYL ALCOHOL FROM CELLULOSIC SUBSTRATES

[75] Inventor: Henri C. Rothlisberger, Beaulieu sur Mer, France

[73] Assignee: Les Services de Consultation D.B. Plus Limitee, Laval, Canada

[21] Appl. No.: 576,738

[22] Filed: Feb. 3, 1984

[51] Int. Cl.$^4$ .......................... A23K 1/12; C12P 7/04; C12R 1/01; D21C 3/20

[52] U.S. Cl. .................................... 435/157; 435/822; 426/53; 162/72; 162/77; 162/79

[58] Field of Search ....................... 435/95, 96, 98, 99, 435/157, 274, 277, 822; 426/2, 53, 807; 162/77, 72, 79

[56] References Cited

U.S. PATENT DOCUMENTS

| | | | |
|---|---|---|---|
| 2,096,377 | 10/1937 | Loughlin | 435/150 |
| 2,420,998 | 5/1947 | Beesch et al. | 435/157 |
| 3,479,249 | 11/1969 | Kalisch | 162/72 |
| 3,990,944 | 11/1976 | Gauss et al. | 435/165 |
| 3,990,945 | 11/1976 | Huff et al. | 435/99 |
| 4,004,967 | 1/1977 | Swan et al. | 162/72 |
| 4,009,075 | 2/1977 | Hoge | 435/162 |
| 4,520,105 | 5/1985 | Sinner et al. | 162/72 |

FOREIGN PATENT DOCUMENTS 1162867 2/1984 Canada .................. 435/157

Primary Examiner—Blondel Hazel
Assistant Examiner—Elizabeth C. Weimar
Attorney, Agent, or Firm—Bacon & Thomas

[57] ABSTRACT

A process for producing isopropyl alcohol and useful by-products from cellulosic substrates without utilizing toxic acids. This process comprises the steps of: (1) digesting cellulosic substrates in a heated solution of sodium carbonate; (2) digesting the cellulosic product of step (1) in a heated solution containing isopropyl alcohol or aluminum isopropylate together with sodium acetate and optionally, acetic acid, to produce a biomass and a black liquid of saturated acyclic hydrocarbons; (3) mixing the biomass of step (2) with amylolytic enzymes or with xylophagous bacteria to initiate fermentation of the biomass; (4) adding the black liquid of step (2) together with basic aluminate acetate and a mixture of formaldehyde and phenol or sulfonated phenol to the mixture of step (3) and heating the resulting mixture to a temperature ranging between 120° to 160° C. under a pressure ranging between 1.5 and 45 kg/cm$^2$ until isopropyl alcohol is produced.

14 Claims, 1 Drawing Figure

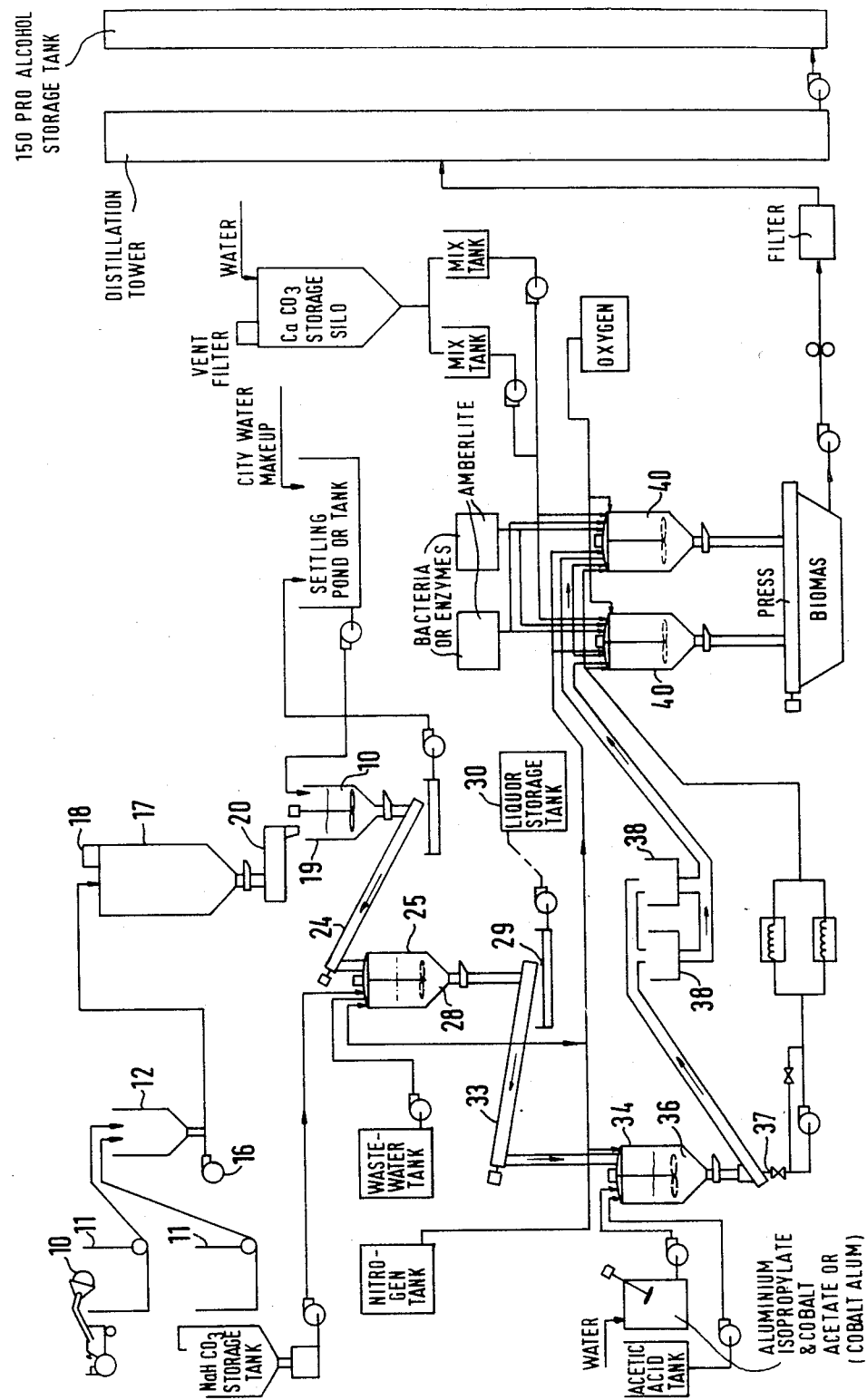

PROCESS FOR PRODUCING ISOPROPYL ALCOHOL FROM CELLULOSIC SUBSTRATES

The present invention relates in general to the production of isopropy alcohol from cellulosic substrates and more specifically to a process that requires less than five hours to produce such alcohol.

The world's supply of oil as a source of energy, especially gasoline for use in internal combustion engines, has become limited and exhaustion of the supply is inevitable. Thus, it is necessary to develop alternative sources of energy. More specifically, liquid fuels which may be used either alone or as a proportionate part with gasoline for driving internal combustion engines are urgently needed. The raw materials used in the production of such alternative sources of energy must be readily available and the cost of the process of making the new fuel in terms of energy and material and processing expense must be such that the process is commercially feasible and the cost of the resulting product within reason.

Very large quantities of surplus and waste cellulosic substrate materials are not only available but often present problems of disposal. Wood refuse of all kinds, including sawdust, chips and woody debris, agricultural materials left after harvesting, such as straw, corn stalks and leaves, etc., are available in large quantity, and readily grown grasses and other plant materials, such as alfalfa and other crops produced for hay, can be employed as very useful raw materials in alcohol producing processes without interfering with normal agricultural food production.

Various types of fermentation processes have been disclosed in U.S. Pat. Nos. 2,420,998, 2,096,377, 3,990,944 and 4,009,075, for producing various types of alcohol from cellulosic materials. However, none of the processes disclosed therein are capable of being performed in less than approximately two days.

The object of the present invention is to provide an improved process for producing isopropyl alcohol from cellulosic substrates including agriculturally produced materials such as cotton, wood, straw and corn stalks, and other substances composed primarily of cellulose such as various types of paper products.

The process according to the invention makes use of cellulosic waste, surplus, or readily producible raw materials for the production of isopropyl alcohol which can be used, preferably in the ratio of one part of alcohol to two parts of gasoline, as a fuel for internal combustion engines without special adjustment of normal gasoline-fueled engines. With some engine alteration, the isopropyl alcohol can be used in larger proportion and in some instances even without intermixing with gasoline.

The process according to the invention requires only a small fraction of the time normally required by the known fermentation processes and only an acceptable amount of energy and quantities of reagent and catalytic material. Contributing to the favorable economics of the process is the production of such useful by-products as protein for animal or human consumption, cattle feed and kraft paper.

The process according to the invention basically comprises digestion of the raw and in-process materials at elevated temperatures and pressures with aqueous solutions of reagent chemicals and catalysts. At no time during the process are toxic acids used.

More particularly the process according to the invention comprises the steps of:

(a) digesting cellulosic substrates in a heated solution of sodium carbonate to hydrolize cellulose from lignin in the cellulosic substrates, and separating the hydrolized cellulose from a first black liquid containing the lignin;

(b) digesting the hydrolized cellulose of step (a) in a heated solution containing aluminum isopropylate or isopropyl alcohol together with sodium acetate and optionally acetic acid, to produce a biomass and a second black liquid of saturated acyclic hydrocarbon;

(c) mixing the biomass of step (b) with a fermentation initiating agent selected from the group consisting of xylophagons bacteria and amylolytic enzymes to initiate fermentation of the biomass; and (d) adding the second black liquid of saturated acyclic hydrocarbons obtained in step (b) together with basic aluminate acetate and a mixture of formaldehyde and phenol or sulfonated phenol to the mixture of step (c) and heating the resulting mixture to a temperature ranging between 120° and 160° C. under a pressure ranging between 1.5 and 45 $kg/cm^2$ until isopropyl alcohol is produced.

As can be understood, the process according to the invention thus is carried out in four separate steps. The first step consists in separating the lignin from the cellulose and in initiating at least to some extent hydrolyzation of the latter. The second step consists in converting a substantial part of the cellulose into a biomass. The third step consists in initiating fermentation of the biomass. Last of all, the fourth step consists in accelerating the fermentation of the biomass under the influence of a chemical environment, to produce isopropyl alcohol.

The chemical materials employed in the process are selected to avoid contamination when discharged and valuable by-products may be recovered, thereby minimizing problems of process waste disposal and contributing positively to the economics of the process.

The invention will be better understood with reference to the following non-restrictive description of a preferred embodiment of the invention, taken in connection with the accompanying drawing in which FIG. 1 is a diagrammatic flow-shart illustrating the process of the present invention.

Referring to FIG. 1, the process first comprises dumping a cellulosic substrate material 10 into either of two grinders 11 connected in parallel to insure that a sufficient amount of starting material 10 is provided to a receiver 12. The grinders 11 are designed to crush the substrate material 11 into small particles having approximately 2–3 cm in length. A blower 16 is connected to the receiver 12 and used for delivering the crushed cellulosic material 10 to a storage silo 17 having a bin filter 18. The bin filter may advantageously be connected to a steam generating system (not shown) that is fueled by dust and minute particles of the material 10 exhausted from the silo 17. In this way, steam is produced for generating the electricity required for performing the process, while the hazard of dust explosions in the silo 17 is substantially eliminated.

The crushed cellulosic material 10 is metered from the silo 17 into a mixing bin 19 by means of a weigher 20, and is thoroughly washed with water to further eliminate dust and minute particles, and to add moisture to the material 10. The washed and humidified material 10 is then delivered by an auger 24 to a first mixer/autoclave 25 to begin the first step of the process of the present invention. Approximately 3 liters of preheated water 37° C., for example and 30 to 150 grams, preferably 40 grams, of sodium carbonate per kilogram of dry weight cellulosic material 10 is added to the autoclave 25 and is heated with such material 10 at a temperature of approximately 110°–135° C., preferably 120° C., for approximately 50–60 minutes. To speed up digestion of the material in the autoclave 25 and also improve the stability of the process, the autoclave 25 may be pressurized under nitrogen at a pressure ranging between 1.5 and 45 kg/cm$^2$. Sodium carbonate is also employed for purposes of stabilization.

The resulting products of the first process step are approximately 70% cellulosic biomass 28 and 30% black liquid 29. This black liquid which contains the lignin is drained off of the biomass 28 for delivery to a storage tank 30. The lignin containing liquid 29 contains recoverable protein and numerous minerals, making is useful for plant fertilizers, or animal and fish food. The remaining cellulosic biomass 28 is thoroughly washed with water and is transferred by an auger 33 to a second mixer/autoclave 34 in which is carried out the second step of the process according to the present invention.

A water solution containing 3 liters of preheated water (37° C., for example), about 30–150 grams of sodium acetate and about 25 to 55 grams of aluminium isopropylate or, alternatively, 20–50 grams, preferably 27 grams, of isopropyl, alcohol is added to the cellulosic biomass 28 in the autoclave 34 for each kilogram dry weight thereof to prevent production of ethanol, and the mixture is digested for about 50–60 minutes preferably 55 minutes, at a temperature ranging from 120°–160° C. To improve the digestion, approximately 5 to 20 grams preferably 7 grams of acetic acid may be added to the water solution. Again, for the purposes of process speed and stabilization, heating may be performed under nitrogen atmosphere at a pressure ranging from 1.5 to 45 kg/cm$^2$. The products of this second process step are another biomass 36 approximately equal to the original amount of cellulosic biomass 28 and a small amount of a second black liquid 37 which is separated from the biomass 36 for later use in the process.

Before beginning the third step of the process, the biomass 36 is conveyed to a pair of parallel arranged coolers 38 for washing, and the black liquid 37 is passed through parallel arranged heat exchangers to reduce the temperatures of the biomass 36 and the liquid 37 to approximately 37° C., which is a preferred temperature for initiating fermentation of the biomass 36. After cooling, the biomass 36 is supplied to one of a parallel pair of third mixer/autoclaves 40, where it is mixed with approximately 40 grams of a fermentation initiating agent which can be zylophagous bacteria or, alternatively amylolytic enzymes. If desired, approximately 100 grams of calcium carbonate may also be added to the biomass to obtain an optimum yield of isopropyl alcohol. The pair of autoclaves 40 are used only one at a time so that batches of product may be fed alternatively from the autoclave 34 to the autoclaves 40 to compensate for the fact that the process steps performed in the autoclaves 40 take longer than the process performed in the autoclave 34.

The remaining two steps of the process both involve fermentation of the biomass 36 and heating of the biomass 36 under pressure regardless of whether bacteria or enzymes are employed. However, there are some differences in the third step depending upon whether bacteria or enzymes are employed as are detailed hereinafter.

Describing first the use of bacteria, the xylophagous bacteria are found in and taken from the flora of the intestines of termites. Cultures of this bacteria produce the bacteria fermentation agent in quantity sufficient for use in the process of this invention. Because of problems involved in storing and maintaining the living bacteria in optimum fermentation producing condition, the use of the amylolytic enzymes is preferred.

After adding 40 grams of the bacteria to the biomass 36 in the autoclave 40, the resulting mixture is heated approximately 35 minutes up to a temperature in the range of about 25°–40° C. (preferably 38° C.) to initiate fermentation, which completes the third process step.

Describing now the use of enzymes in the process steps 3 and 4, the fermentation produced is aerobic and, consequently, the autoclave 40 must be pressurized during such steps by oxygen rather than nitrogen. To begin process step 3, 40 grams of amylolytic enzymes are added to the biomass 36 per each kilogram of its dry weight, and the pH of the resulting mixture is adjusted to a range of 5.8–6.4.

The resulting mixture is then heated for approximately 35 minutes to a temperature in the range of approximately 30°–40° C. (preferably 38° C.) either in open air or under pressurized oxygen atmosphere to initiate fermentation, which completes the third process step. During this step, pH of the mixture preferably falls in a range of 6.2–6.4.

The fourth step of the process of the present invention is begun by adding to the autoclave 40, per kilogram of dry weight glucose biomass 36, 10–30 grams of aluminum acetate, 100–200 grams of a mixture containing about 65% of formaldehyde and 35% of phenol or sulfonated phenol and the cooled black liquid 37. To increase the efficiency of process steps 3 and 4 when employing bacteria as the fermenting agent, it is highly preferable to also add approximately 40 grams of cobalt acetate per kilogram of the dry weight of the biomass 36. Thereafter the mixture in the autoclave 40 is progressively heated up to 120°–160° C. under a nitrogen atmosphere up to a pressure ranging from 1.5 to 45 kg/cm$^2$. Heating at this temperature and pressure is continued for 55 minutes, at which time heating is discontinued to complete process step 4.

At the end of the fourth process step, the isopropyl alcohol is formed and the liquid resulting therefrom is filtered and distilled to separate the isopropyl alcohol from the water mass. The remaining fibrous biomass material is pressed to extract as much as possible of the alcoholcontaining liquid. The biomass material remaining may then be washed and used either as a readily digestable cattle feed or in the manufacture of kraft paper products. The amount of alcohol obtained is equal in weight to approximately 40 percent of the dry weight of the original biomass present at the beginning of process step 3.

Thus, the entire process of the present invention can be completed in less than five hours which is in sharp contrast to all similar type prior art processes the durations of which are in terms of days. The key ingredient for obtaining such a significant reduction in process time is the utilization in the fourth process step of a catalyst consisting of aluminum acetate and of a mixture of formaldehyde and phenol or sulfonated phenol. The addition of such a catalyst in the fourth step produces an immediate chemical reaction.

Following below are a number of examples of the process of the present invention, which examples are described for purposes of illustration only and not limitation.

EXAMPLE 1

Step 1. 1 Kg. of crushed straw was washed with water at 37° C. for about 10 minutes and placed in a mixer/autoclave. 3 liters of water containing 40 grams of sodium carbonate was added. The autoclave was closed and heat applied. Nitrogen gas was connected to the autoclave and supplied at a minimum pressure of 1.5 kg/cm$^2$ and the mixture was heated to a temperature of 120° C. for 55 minutes. Heat was then discontinued and the autoclave opened. A first black liquid was poured off and the straw washed with water.

Step 2. The treated straw was replaced in the autoclave and 40 grams of sodium acetate, 27 grams of isopropyl alcohol and 7 grams of acetic acid mixed in 3 liters of water preheated at 37° C. was added thereto. Heat was applied and nitrogen gas under pressure supplied to the autoclave. The temperature of the mixture was raised to about 120° C. with the nitrogen pressure maintained over 1.5 kg/cm$^2$ for about 55 minutes. The autoclave was opened and a second black liquid poured into a container to cool for reuse, the straw was washed with cold water.

Step 3. 40 grams each of xylophagous bacteria and calcium carbonate were mixed with the cooled straw. Heat was turned on and the temperature brought up to 38° C. during 35 minutes.

Step 4. 17 grams of aluminium acetate were dissolved in the black liquid from Step 2 and this mixture was added to the autoclave together with a mixture containing 84.5 grams of formaldehyde and 45.5 grams of phenol. The nitrogen pressure was set at 30 kg/cm$^2$ and temperature of the autoclave was progressively increased to 150° C. The mixture was then maintained at 150° C. for about 55 minutes. Heat was then turned off, pressure released, and liquid containing isopropyl alcohol recovered, filtered and distilled.

EXAMPLE 2

The process as described in Example 1, except that in Step 3, 40 grams of cobalt acetate was also mixed with the straw.

EXAMPLE 3

Step 1. 900 grams of straw were broken up, washed and placed in a mixer/autoclave. 60 grams of sodium carbonate were dissolved in 3 liters of water and the solution poured over the straw. Heat was turned on and the temperature gradually increased in the course of one hour to 124° C. The heat was turned off, the autoclave opened and a first black liquid poured off. The straw was washed with tap water.

Step 2. The straw was replaced in the autoclave and 40 grams of sodium acetate, 32 grams of aluminum isopropylate and 10 grams of acetic acid were slurried with 3 liters of water at 37° C. The slurry was poured on top of the straw and mixed in. The autoclave was closed and heat was turned on. The temperature after 55 minutes was 160° C. and the pressure close to 45 kg/cm$^2$. At this time the heat was turned off and a second black liquid poured from the autoclave into a container.

Step 3. The straw was cooled by washing with running water and 40 grams of amylolytic enzymes were mixed with the straw. This mixture was placed in the autoclave and was heated to a temperature of 39° C. for about 30 minutes in open air.

Step 4. 120 grams of a mixture of formaldehyde and sulfonated phenol (phenol blue) were mixed with water and added to the straw material. 20 grams of aluminium acetate was added to the second black liquid and this solution was poured into the autoclave. Heat was increased to 120° C. and then maintained for the next 55 minutes, after which the heat was turned off, the pressure released and a liquid containing the isopropyl alcohol was poured off, filtered and distilled.

I claim:

1. A process for producing isopropyl alcohol from cellulosic substrates which includes the steps of:
   (a) digesting the cellulosic substrates in a heated solution containing from 30 to 150 grams of sodium carbonate per kilogram of dry weight cellulosic substrates to hydrolize cellulose from lignin in the cellulosic substrates, and separating said hydrolized cellulose from a first black liquid containing said lignin;
   (b) digesting the hydrlolized cellulose of step (a) in a heated solution containing about 25 to 55 grams of aluminium isopropylate or 20 to 50 grams of isopropyl alcohol together with 30 to 150 grams of sodium acetate per kilogram of dry weight hydrolized cellulose to produce a biomass and a second black liquid of saturated acyclic hydrocarbons;
   (c) mixing the glucose biomass of step (b) with a fermentation initiating agent selected from the group consisting of xylophagous bacteria and amylolytic enzymes, to initiate fermentation of the biomass;
   (d) adding the second black liquid of saturated acyclic hydrocarbons obtained in step (b) together with 10 to 30 grams of aluminium acetate and 100 to 200 grams of a mixture of formaldehyde and phenol or sulfonated phenol per kilogram of dry weight glucose biomass to the mixture of step (c), and fermenting by heating the resulting mixture to a temperature ranging from 120° to 160° C. for sufficient time to produce isopropyl alcohol and wherein steps (c) and (d) are conducted under an inert atmosphere when said fermentation initiating agent is bacteria, and under an oxygen-containing atmosphere when said initiating agent is an enzyme, and the selected atmosphere in step (d) has a pressure ranging from 1.5 to 45 kg/cm and;
   (e) isolating isopropyl alochol from the liquid resulting from step (d).

2. A process according to claim 1 wherein step (a) is carried out in an autoclave under a pressure ranging from 1.5 kg/cm$^2$ to 45 kg/cm$^2$.

3. A process according to claim 2, wherein step (a) is carried out for about 55 minutes.

4. A process according to claim 1 wherein acetic acid is added to the heated solution used in step (b).

5. A process according to claim 4, wherein step (b) is carried out in an autoclave under an inert atmosphere.

6. A process according to claim 5, wherein step (b) is carried out for at least 55 minutes.

7. A process according to claim 1 wherein the fermentation initiating agent used in step (c) is xylophagous bacteria.

8. A process according to claim 7 wherein calcium carbonate is added to and mixed with the biomass in step (c).

9. A process according to claim 8, wherein cobalt acetate is added to the second black liquid prior to carrying out step (d).

10. A process according to claim 1 wherein the fermentation initiating agent is amylolytic enzymes.

11. A process according to claim 10 wherein calcium carbonate is added to and mixed with the biomass in step (c).

12. A process according to claim 1 wherein the fermentation initiating agent is bacteria.

13. A process according to claim 12, wherein the mixture of formaldehyde and phenol or sulfonated phenol used in step (d) comprises 65% by weight of formaldehyde and 35% by weight of phenol or sulfonated phenol.

14. A process according to claim 13, wherein the mixture comprises formaldehyde and phenol.

* * * * *